United States Patent
Gia

Patent Number: 6,099,546
Date of Patent: Aug. 8, 2000

[54] DETACHABLE EMBOLIC COIL ASSEMBLY USING INTERLOCKING HOOKS AND SLOTS

[75] Inventor: Son Gia, San Jose, Calif.

[73] Assignee: Target Therapeutics, Inc., Fremont, Calif.

[21] Appl. No.: 08/782,584

[22] Filed: Jan. 13, 1997

Related U.S. Application Data

[62] Division of application No. 08/400,471, Mar. 7, 1995, which is a continuation of application No. 08/049,577, Apr. 19, 1993, abandoned.

[51] Int. Cl.[7] .................................................. A61B 17/12
[52] U.S. Cl. .......................................... 606/191; 606/200
[58] Field of Search ............................ 128/899; 606/108, 606/116–117, 191, 195, 198; 604/57, 59, 60, 62, 891.1, 892.1

[56] References Cited

U.S. PATENT DOCUMENTS

| | | |
|---|---|---|
| 3,334,629 | 8/1967 | Cohn . |
| 3,789,841 | 2/1974 | Antoshkiw . |
| 4,545,390 | 10/1985 | Leary . |
| 4,619,274 | 10/1986 | Morrison . |
| 4,739,768 | 4/1988 | Engelson . |
| 4,781,177 | 11/1988 | Lebigot . |
| 4,813,934 | 3/1989 | Engelson et al. . |
| 4,832,055 | 5/1989 | Palestrant ................................ 128/899 |
| 4,884,579 | 12/1989 | Engelson ................................ 128/772 |
| 4,957,501 | 9/1990 | Lahille et al. . |
| 4,994,069 | 2/1991 | Ritchart et al. . |
| 5,002,556 | 3/1991 | Ishida et al. . |
| 5,062,829 | 11/1991 | Pryor et al. . |
| 5,064,434 | 11/1991 | Habert . |
| 5,098,374 | 3/1992 | Othel-Jacobsen et al. . |
| 5,098,440 | 3/1992 | Hillstead . |
| 5,108,407 | 4/1992 | Geremia et al. ........................ 606/108 |
| 5,109,867 | 5/1992 | Twyford, Jr. . |
| 5,122,136 | 6/1992 | Guglielmi et al. ........................ 606/32 |
| 5,133,731 | 7/1992 | Butler et al. . |
| 5,167,624 | 12/1992 | Butler et al. . |
| 5,174,276 | 12/1992 | Cockard . |
| 5,192,301 | 3/1993 | Kamiya et al. . |
| 5,217,484 | 6/1993 | Marks ..................................... 606/200 |
| 5,234,437 | 8/1993 | Sepetka ................................... 606/108 |
| 5,250,071 | 10/1993 | Palermo ................................. 606/198 |
| 5,261,916 | 11/1993 | Engelson ................................ 606/108 |
| 5,263,964 | 11/1993 | Purdy . |
| 5,304,195 | 4/1994 | Twyford, Jr. et al. ................... 606/191 |
| 5,312,415 | 5/1994 | Palermo . |
| 5,350,397 | 9/1994 | Palermo et al. . |
| 5,354,295 | 10/1994 | Guglielmi et al. . |
| 5,423,829 | 6/1995 | Pham et al. . |
| 5,522,836 | 6/1996 | Palermo . |
| 5,540,680 | 7/1996 | Guglielmi et al. . |
| 5,601,600 | 2/1997 | Ton et al. . |
| 5,733,294 | 3/1998 | Forber et al. . |
| 5,743,905 | 4/1998 | Eder et al. . |
| 5,800,453 | 9/1998 | Gia . |

(List continued on next page.)

FOREIGN PATENT DOCUMENTS

| | | |
|---|---|---|
| 0341039 | 8/1989 | European Pat. Off. . |
| WO 97/48351 | 12/1997 | WIPO . |
| WO 98/02100 | 1/1998 | WIPO . |
| WO 98/04198 | 2/1998 | WIPO . |
| WO 98/04315 | 2/1998 | WIPO . |

*Primary Examiner*—Michael Buiz
*Assistant Examiner*—Vikki Trinh
*Attorney, Agent, or Firm*—Morrison & Foerster LLP

[57] ABSTRACT

This invention is a surgical instrument and specifically is a device for delivering embolic coils to a selected site within the vasculature or other lumen of a human body via use of a catheter. The invention includes the coils as well. In particular, the device uses embolic coils having a receiving slot on one end of the coil; a catheter control wire or pusher guidewire having a hook which cooperatingly engages the coil's receiving slot is used as a coil pusher to eject the coil at the chosen site. The coils of this invention may also be placed within the lumen with a catheter in a nose-to-tail fashion and pushed into the body lumen. Pushing the coil assembly via the pusher from the distal end of the catheter body uncouples the most distal coil.

4 Claims, 3 Drawing Sheets

U.S. PATENT DOCUMENTS

| | | |
|---|---|---|
| 5,800,454 | 9/1998 | Jacobsen et al. . |
| 5,855,578 | 1/1999 | Guglielmi et al. . |
| 5,891,128 | 4/1999 | Gia et al. . |
| 5,891,130 | 4/1999 | Palermo et al. . |
| 5,895,385 | 4/1999 | Guglielmi et al. . |
| 5,895,391 | 4/1999 | Farnholtz . |
| 5,911,717 | 6/1999 | Jacobsen et al. . |
| 5,916,235 | 6/1999 | Guglielmi . |
| 5,919,187 | 7/1999 | Guglielmi et al. . |
| 5,925,037 | 7/1999 | Guglielmi et al. . |
| 5,925,060 | 7/1999 | Forber . |
| 5,925,062 | 7/1999 | Purdy . |
| 5,928,226 | 7/1999 | Guglielmi et al. . |
| 5,944,714 | 8/1999 | Guglielmi et al. . |
| 5,944,733 | 8/1999 | Engleson . |

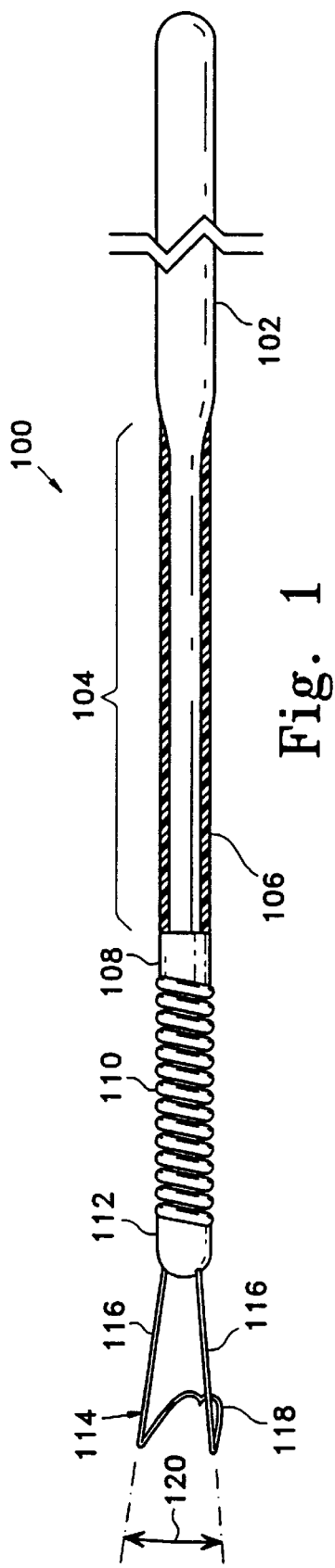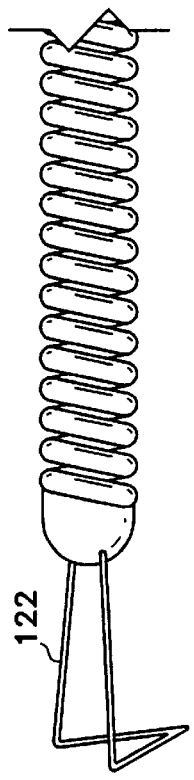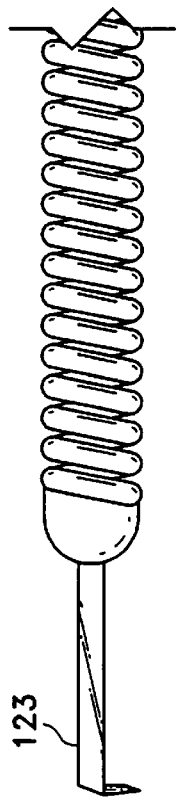

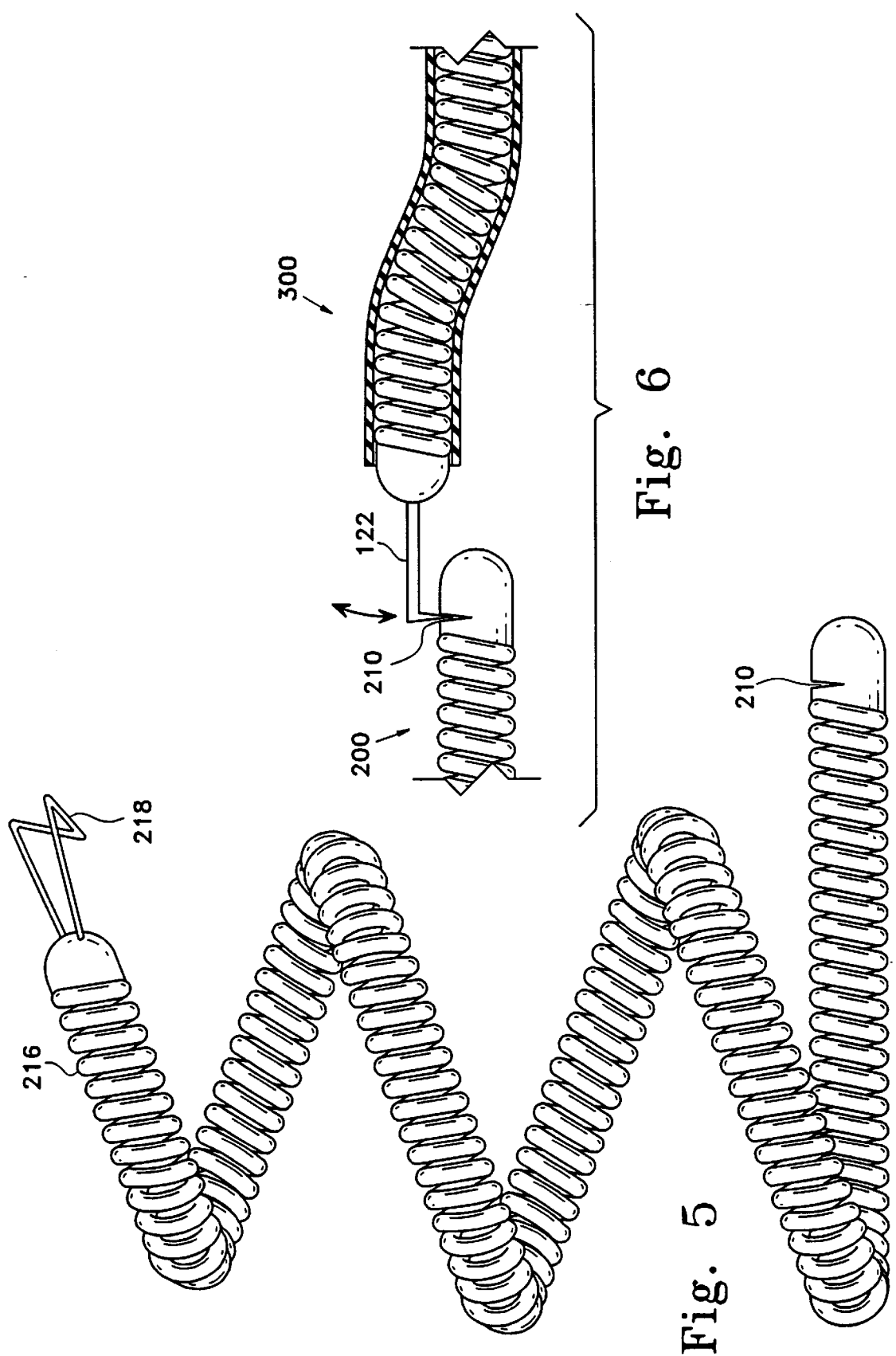

DETACHABLE EMBOLIC COIL ASSEMBLY USING INTERLOCKING HOOKS AND SLOTS

This application is a divisional of application Ser. No. 08/400,471, allowed filed Mar. 7, 1995, pending, which is a continuation of application Ser. No. 08/049,577, filed Apr. 19, 1993, abandoned.

FIELD OF THE INVENTION

This invention is a surgical instrument and specifically is a device for delivering embolic coils to a selected site within the vasculature or other lumen of a human body via use of a catheter. The invention includes the coils as well. In particular, the device uses embolic coils having a receiving slot on one end of the coil; a catheter control wire or pusher guidewire having a hook which cooperatingly engages the coil's receiving slot is used as a coil pusher to eject the coil at the chosen site. The coils of this invention may also be placed within the lumen with a catheter in a nose-to-tail fashion and pushed into the body lumen. Pushing the coil assembly via the pusher from the distal end of the catheter body uncouples the most distal coil.

BACKGROUND OF THE INVENTION

The endovascular treatment of a variety of vascular maladies throughout the body is an increasingly more important form of therapy. Catheters have been used to place various treatment materials, devices, and drugs within arteries and veins in the human body. Examples of these devices and their use in such treatments are shown in U.S. patent application Nos. 07/806,898 ("Detachable Pusher-Vasoocclusive Coil Assembly with Threaded Coupling"); 07/806,912 ("Detachable Pusher-Vasoocclusive Coil Assembly with Interlocking Ball and Keyway Coupling"); and 07/949,094 ("Detachable Embolic Coil Assembly Using Interlocking Clasps"). These documents show methods and devices for delivery of coils or wires within the human body to sites such as aneurysms, to occlude those sites. Coils such as are discussed in those documents (as well as in U.S. Pat. No. 4,994,069), may be of a regular or helical configuration or assume a random convoluted configuration at the site. The coils normally are made of a radiopaque, biocompatible metal such as platinum, gold, tungsten, or alloys of these and other metals.

In treating aneurysms it is common to place a number of coils within the aneurysm. The coils occlude the site by posing a physical barrier to blood flow and by promoting thrombus formation at the site.

Coils have typically been placed at the desired site within the vasculature using a catheter and a pusher. The site is first accessed by the catheter. In treating vascular conditions requiring occlusion, the sites are accessed with flexible, small diameter catheters such as those shown in U.S. Pat. Nos. 4,739,768 and 4,813,934. The catheter may be guided to the site through the use of guidewires (see, U.S. Pat. No. 4,884,579) or by flow-directed means such as balloons placed at the distal end of the catheter. Use of guidewires involves the placement of relatively long, torqueable proximal wire sections within the catheter, which wire has a more flexible distal end wire section designed to be advanced across sharp bends at vessel junctions. The guidewire is visible using x-ray-and allows a catheter to be manipulated through extremely tortuous vessels, even when such vessels are surrounded by soft tissue such as the brain.

Once the site has been reached, the catheter lumen is cleared by removing the guidewire (if a guidewire has been used), and the coil is placed into the proximal open end of the catheter and advanced through the catheter with a pusher. Pushers are wires having a distal end that is adapted to engage and push the coil through the catheter lumen as the pusher is advanced through the catheter. When the coil reaches the distal end of the catheter, it is discharged from the catheter by the pusher into the vascular site. Although this technique of discharging the coil from the distal end of the catheter has a number of undesirable limitations, it has the benefit of low cost a short delivery time for multiple coils.

Several techniques have been developed to enable more accurate placement of coils within a vessel. In one technique (U.S. Pat. No. 5,122,136, issued Jun. 16, 1992) the coil is bonded via a metal-to-metal joint to the distal end of the pusher. The pusher and coil are made of dissimilar metals. The coil-carrying pusher is advanced through the catheter to the site and a small electrical current is passed through the pusher-coil assembly. The current causes the joint between the pusher and the coil to be severed via electrolysis. The pusher may then be retracted leaving the detached coil at an exact position within the vessel. In addition to enabling accurate coil placement, the electric current may facilitate thrombus formation at the coil site. The only perceived disadvantage of this method is that the electrolytic release of the coil requires a period of time so that rapid detachment of the coil from the pusher does not occur.

Another technique for detaching an embolic coil is shown in U.S. patent application 07/806,912. In that document, a coil having an enlarged portion is mated with a pusher having a keyway adapted to receive the enlarged portion of the coil in an interlocking relationship is covered by a coaxial member about the pusher and the coil. The coaxial member is movable by sliding the member axially. As the coaxial member is moved away from the junction where the coil's member engages the member of the keyway of the pusher, the coil disengages and the pusher is removed.

Another device for placement of coils is shown in U.S. patent application 07/806,898. This device includes a coil having a helical portion at one end and a pusher which is threaded to the inside of the helical coil by the use of a threaded section on the outside of the pusher. The device operates to release the coil by engaging the proximal end of the coil with a sleeve while the pusher is unthreaded. Once the pusher is free, the sleeve may be used to push the coil out into the treatment area.

U.S. patent application 07/949,049 shows an embolic coil having engageable ramps at the end of the coil and having a passageway through the axis of the coil and through the ramps. The axial passageway serves as a path for a central wire which locks the various coils together or the coil with the catheter.

Still another method of placing an embolic coil is shown in U.S. Pat. No. 5,108,407. This patent shows the use of a device in which embolic coils are separated from the distal end of a catheter by the use of heat-releasable adhesive bonds. The coil adheres to the therapeutic device via a mounting connection using a heat sensitive adhesive. Laser energy is transferred through a fiber optic cable, which cable terminates at the connector. The connector becomes warm and releases the adhesive bond between the connector and the coil.

None of these disclosed devices suggest the use of an interlocking hook which allows an embolic coil to be precisely positioned and then released upon ejection of the coil from the catheter distal end.

SUMMARY OF THE INVENTION

This invention is a device for placing detachable embolic coils within the vasculature of the human body so to occlude that site using the coils. This device includes a coil that carries receiving slot on at least one end of the coil, preferably at its proximal end. The device also includes a pusher which is typically positioned within the catheter and which pusher has, at its distal end, a hook which is shaped in such a way that it engages the receiving slot within the embolic coil. An alternative variation includes coils having at their distal ends engaging hooks similar to that described in conjunction with the guidewire pusher. In this way a number of coil segments may be introduced into one or more vascular sites by ejecting the most distal coil from the end of the catheter as needed.

Another portion of the invention involves the method for occluding the selected vascular site comprising the steps of: (a) accessing the site with the distal end of a catheter; (b) advancing the coil assembly mentioned above through the lumen of the catheter to the selected site; (c) using a guidewire having an engageable hook at its distal end to push a coil having a coordinated, engageable slot at its proximal end out into the selected vascular site; (d) disengaging the hook from the engageable slot in the coil; and (e) removing the catheter body from the human subject.

BRIEF DESCRIPTION OF THE DRAWINGS

FIG. 1 shows in partial cross-sectional view, a guidewire pusher assembly having a W-shaped hook at the distal end for engaging coils having a cooperatively shaped slot.

FIG. 2 shows the distal tip of a variation of the guidewire pusher shown in FIG. 1 but having a simply V-shaped hook positioned at the distal end.

FIG. 3 shows the distal tip of a variation of the guidewire pusher shown in FIG. 1 but having a solid hook positioned at the distal end.

FIG. 5 shows a coil similar in construction to that found in FIG. 4, but also having a hook at its other end.

FIG. 6 depicts the manner in which the invention operates.

DESCRIPTION OF THE INVENTION

Figure 4:
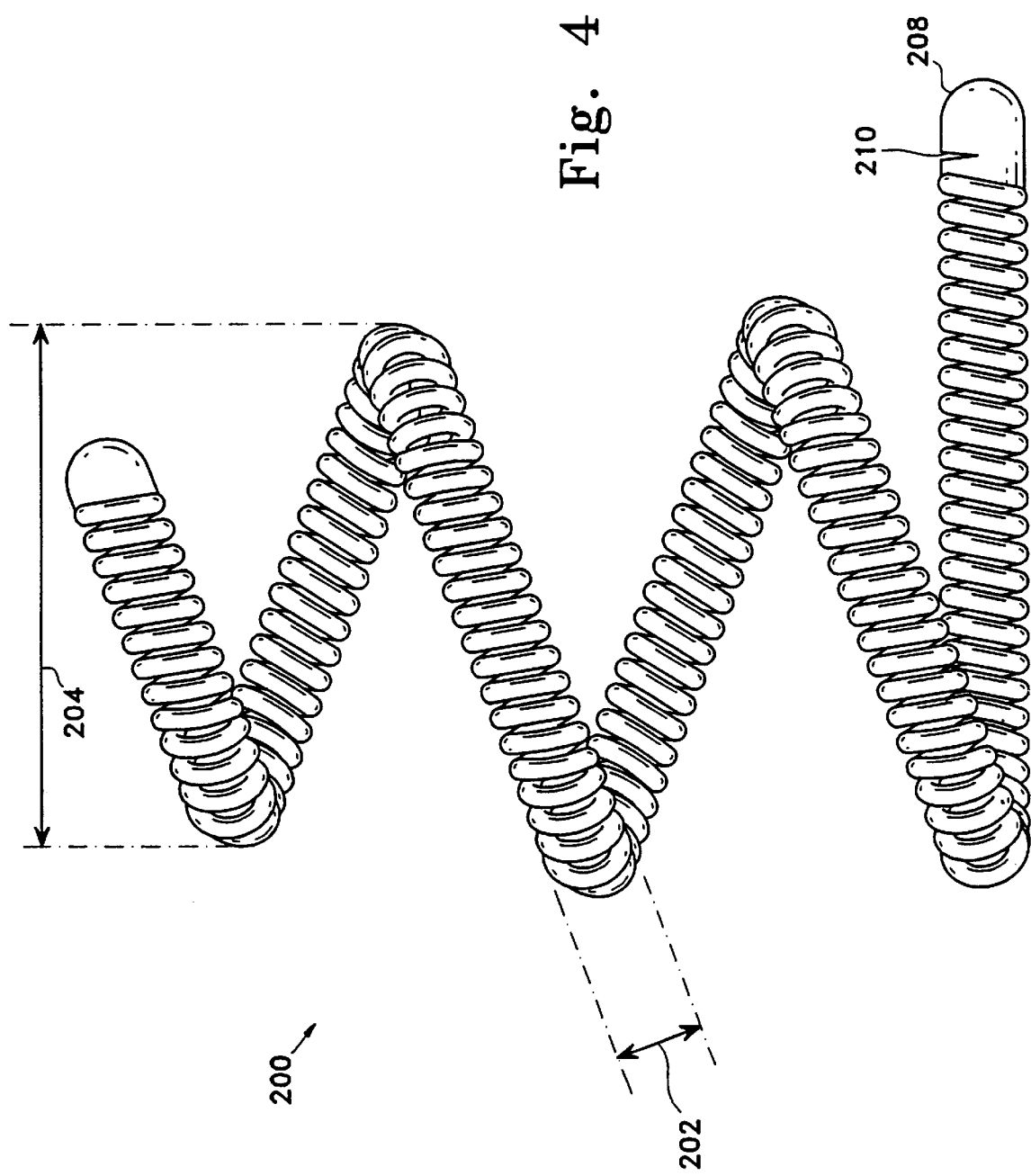
FIG. 4 shows an embolic coil having the desired engaging slot at one end.

The pusher assembly (100) is shown in FIG. 1. The configuration of the body of the pusher assembly (100) is not particularly critical, and many variations known in the art would likely be suitable. The variation shown here entails, at the distal end, a stainless steel core (102) having a smaller diameter section (104) covered by a desired polymeric material (106) such as tetrafluoroethylene, or other suitable fluorinated hydrocarbon polymers; hydrophilic polymers such as polyvinylpyrrolidone, polyethyleneoxide, or polyhydroxyethylmethacrylate, or copolymers, or mixtures, or blends thereof; or various silicone-based polymeric materials; or polyolefins such as polyethylene, polypropylene, or their copolymers, mixtures, or blends; or appropriate polyurethane polymers. This coating provides a slippery surface allowing ease of insertion and traverse through the catheter body.

It is desirable to include a radiopaque marker (108). Such markers are common in this art and may be made of known radiopaque materials such as platinum, palladium, or other such materials. Commonly, the radiopaque marker (108) is a coil which is brazed or soldered to the guidewire and may be coated with the polymeric materials (106). This marker allows the tending physician to monitor the progress of the guidewire tip via fluoroscopy and, obviously, allow proper placement of the coil which is attached to the end of the pusher guidewire (100).

More distal of the radiopaque marker (108) may be found a flexible coil (110). This coil covers a tapered section of the core wire (102). Tapering the inner wire and enclosing it in a wire coil increases the column strength of the tapered wire section without significant loss of flexibility and increases the radial capacity of the guidewire to allow fine manipulation of the guidewire through various tortuous portions of the vasculature. The tip of the core wire (102) and the distal portion of the wire coil (110) are typically joined by use of a solder joint (112). To this point, the guidewire is of a typical guidewire respected in this art. See, for instance, those guidewires shown in U.S. Pat. Nos. 3,789,841; 4,545,390; and 4,619,274.

Unique to this invention is the hook (114) placed at the most distal end of the guidewire assembly (100) which transforms it into a pusher.

Engaging hook (114) has two legs (116) which are based in solder joint (112). The outer hook portion (118) is configured so that it slides into the conforming slot in the coils discussed below. The diameter (120) of the hook (114) is typically no larger than the inside diameter of the catheter assembly into which it is placed. Obviously, if the diameter is larger, it will bind in the catheter and be of little use. The most distal portion of the hook (118) is configured in such a way that the "W" portion is in a plane which is generally perpendicular to the longitudinal axis of the guidewire pusher assembly (100). The engaging hook (114) need be made only of a material which is adequate under the circumstances of use. For instance, the hook may be of a stainless steel wire which may be soldered onto the end of the guidewire assembly (100) and bent into desirable shape. In this way, the hook may be used to push the attached coil through the catheter without bending. The length of guidewire pusher assembly (100) should be such as to be capable of being advanced entirely through a catheter to place a coil such as shown in FIGS. 4 and 5 at the target site, but yet retain a sufficient portion of the proximal end of the guidewire pusher assembly (100) protruding from the proximal end of the catheter to enable the pusher to be manipulated. For use in peripheral and neural surgeries, the pusher will normally be about 100–200 cm in length, more normally 130–180 cm in length. The diameter of the guidewire pusher assembly (100) is usually in the range of 0.25 to about 0.90 mm.

FIG. 2 shows a variation of the distal tip of guidewire pusher assembly (100) having a slightly different configuration than that shown in FIG. 1. In this instance, the hook is a simple "V"- or "U"-shaped hook (122) which also will engage with the slotted coils described below. The materials of construction and other such variables are similar to those for the hook of FIG. 2. FIG. 3 shows an additional variation of the pusher assembly (100) having a hooked distal tip. This hook (123) is of a bent ribbon rather than the wire configuration shown in FIGS. 1 and 2. The materials of construction and method of attachment are similar to those used in the FIG. 1 and 2 variations. The ribbon is bent in such a way as to allow insertion of the hook's bent lip into the slot found in the coils discussed below.

The coil typical of that which might be used with this invention, is shown in FIG. 4. The coil (200) is shown as helical in form, although it may be any other suitable form. The coil shown is one having a primary and a secondary diameter. The primary diameter (202) is sufficiently small that the coil (200), when straightened, would fit inside the lumen of the catheter assembly. The coil assembly shown assumes a second diameter (204) when ejected from the tip of the catheter using the pusher guidewire (100) shown in FIG. 1.

Coil (200) is desirably made up of a radiopaque, physiologically compatible material. The material may be platinum, gold, tungsten, or alloys of any or all of these. Certain polymers are also suitable as coil material either alone or in conjunction with metallic markers providing radiopacity. These materials are chosen so that the procedure of locating coils or placing coils within the vascular system may be viewed using fluoroscopy or radiography. However, as also contemplated, these coils may be made of other biologically inert polymers or of carbon fiber.

The size of the coil in its constituent winding will depend upon the use to which the coil will be placed. For occluding vascular sites, the coils would typically be made of 0.05 to 0.15 mm diameter wire (platinum or platinum/tungsten alloy) that is wound to have an inner diameter of 0.15 to 1.5 mm with a minimum pitch—that is to say that the pitch is equal to the diameter of the wire used in the coil. The outer diameter is then typically 0.25 mm to 1.8 mm. The length of the coil used in this configuration may be in the range of 0.5 to 100 cm, preferably 0.5 to 40 cm.

If desired, the coil may be formed in such as way that the coil is essentially linear as it passes through the catheter and yet assumes a randomly oriented, relaxed condition after it is released from the distal end of the catheter. A discussion of such a variation may be found in U.S. Pat. No. 4,994,069, to Richart et al. Richart et al. also shows a variety of other desirable shapes, including figure eights, cloverleaves and the like suitable for this usage.

Whatever the chosen shape may be, the coil typically has caps at each ends Specifically, the distal end of the coil (200) will have a distal cap to (206) which may be solder or epoxy or other filling adhesive or fused from the coil metal, preferably forming a rounded form to prevent the coil from hanging up within the catheter or an inappropriate place within the patient's vasculature. The unique aspect of this invention is found at the proximal end (208) of the coil (200). The proximal end typically will be soldered or glued, much in the way that the distal end has been, but is configured in such a way that a slot (210) is opened during the soldering or gluing process and will accept the hook, variously (114) in FIG. 1 or (122) in FIG. 2 or (123) in FIG. 3 into the slot. Obviously, the receiving slot (210) is generally substantially perpendicular to the local axis of the coil.

FIG. 5 depicts a variation of the coil shown in FIG. 4. This variation, however, includes, at the distal end of the coil (216), a hook (218) of configuration similar to that found in discussing the guidewire pusher assemblies in FIGS. 1 and 2. This configuration allows the introduction of discrete segments of coils into the catheter and separate placement of them should such a situation be desirable. In such an instance, the hook (218) would be introduced into the receiver slot (210) in the similar coil next in line. The most proximal of the coils would, in turn, be engaged with a hook on a guidewire assembly such as (100) shown in FIG. 1.

FIG. 6 is a side view depicting how the hook (122), as depicted here, is placed in slot (210) of the coil assembly (200). The tip of a typical catheter (300) is shown in the figure. Again, the overall diameter of the various assemblies as put together for introduction into or out of catheter must be of a diameter smaller than the diameter lumen in catheter (300). Obviously, too large a coil/pusher combination will not be particularly valuable in a situation where such is needed.

As indicated previously, conventional catheter insertion and navigational techniques involving guidewires or even flow-directed devices may be used to access a chosen vascular site with a catheter. Once the distal end of the catheter is positioned at that chosen site, often by locating its distal end through the use of a radiopaque marker material and radiography, the catheter is cleared. For instance, if a guidewire has been used to position a catheter, it is withdrawn from the catheter and then the guidewire pusher assembly such as (100) shown in FIG. 1 having coil assembly such as (200) in FIG. 4 is assembled and introduced into the proximal end of the catheter. The guidewire pusher assembly is then advanced so that its distal end is free of the distal end of the catheter and the coil positioned precisely at the desired site. The pusher assembly (100) may require a twisting movement to free the distal hook from the receiving slot in the coil.

Modifications of the device described above and methods of using it in keeping with this invention that are apparent to those having skill in this mechanical and surgical instrument design art and related fields are intended to be within the scope of the claims which follow.

I claim as my invention:

1. A method for occluding a selected site in the body's vasculature comprising the steps of:
   a) accessing the selected vascular site with the distal end of a catheter lumen and a pusher assembly consisting essentially of a pusher engaged to a coil assembly, wherein said pusher has an engageable hook on a distal end, said engageable hook having a portion engaged with a slot in an end of said coil assembly;
   b) pushing said pusher assembly to advance said coil assembly through the catheter lumen to the selected vascular site;
   c) advancing said coil assembly out of the distal end of the catheter lumen;
   d) disengaging said engageable hook on said pusher from said coil assembly slot; and
   e) removing the catheter and said pusher from the vasculature.

2. The method of claim 1 where the portion of the engageable hook coordinatively engaging the slot in the coil assembly is "W" shaped.

3. The method of claim 1 where the portion of the engageable hook coordinatively engaging the slot in the coil assembly is "V" shaped.

4. The method of claim 1 where the engageable hook is a bent ribbon.

* * * * *